United States Patent
Fischer

(10) Patent No.: US 8,857,986 B2
(45) Date of Patent: Oct. 14, 2014

(54) DEVICE AND METHOD FOR ACCURATELY DETERMINING THE REAR VERTEX DISTANCE BETWEEN THE EYE AND THE LENSES IN EYEGLASSES

(76) Inventor: Eric Fischer, Oberhaching (DE)

(*) Notice: Subject to any disclaimer, the term of this patent is extended or adjusted under 35 U.S.C. 154(b) by 1329 days.

(21) Appl. No.: 12/430,073

(22) Filed: Apr. 25, 2009

(65) Prior Publication Data
US 2009/0207375 A1 Aug. 20, 2009

Related U.S. Application Data

(63) Continuation-in-part of application No. 11/210,450, filed on Aug. 25, 2005, now Pat. No. 7,540,612.

(30) Foreign Application Priority Data

Oct. 9, 2004 (EP) .................................. 04021588

(51) Int. Cl.
*A61B 3/14* (2006.01)
*G02C 5/00* (2006.01)
*A61B 3/11* (2006.01)
*G02C 13/00* (2006.01)

(52) U.S. Cl.
CPC ............... *G02C 13/005* (2013.01); *A61B 3/11* (2013.01)
USPC ............................................ 351/206; 351/41

(58) Field of Classification Search
USPC ......... 351/200, 205, 206, 221, 222, 220, 243, 351/41
See application file for complete search history.

(56) References Cited

U.S. PATENT DOCUMENTS

| | | | |
|---|---|---|---|
| 4,505,043 A | | 3/1985 | Sztuka |
| 4,744,633 A | * | 5/1988 | Sheiman ..................... 359/465 |
| 5,009,496 A | * | 4/1991 | Holtan et al. ................ 351/156 |
| 5,365,286 A | * | 11/1994 | Masuda ....................... 351/204 |
| 6,771,403 B1 | * | 8/2004 | Endo et al. .................... 359/13 |
| 7,001,020 B2 | * | 2/2006 | Yancey et al. ............... 351/221 |
| 8,220,922 B2 | * | 7/2012 | Chauveau et al. ........... 351/204 |

* cited by examiner

*Primary Examiner* — Thomas K Pham
*Assistant Examiner* — Brandi Thomas
(74) *Attorney, Agent, or Firm* — LaMorte & Associates, P.C

(57) ABSTRACT

A measurement instrument and its associated method of use to record a pupil center position of a person's eye and determine rear vertex distance to a lens. The instrument has a chassis and a free swinging assembly that is pivotably attached to the chassis. The swinging assembly has alignment points that remain in a horizontal plane as the swinging assembly swings. The instrument is attached to a set of eyeglass that are worn on that person's head. A prism is suspended adjacent the eye. The pupil is viewed through the prism. The offset of the viewed image is measured and used to calculate the rear vertex distance.

14 Claims, 4 Drawing Sheets

DEVICE AND METHOD FOR ACCURATELY DETERMINING THE REAR VERTEX DISTANCE BETWEEN THE EYE AND THE LENSES IN EYEGLASSES

RELATED APPLICATIONS

This application is a continuation-in-part of U.S. patent application Ser. No. 11/210,450, filed Aug. 25, 2005 now U.S. Pat. No. 7,540,612, which claims priority of co-pending European Patent Application No. 04021588.1, filed Sep. 10, 2004.

BACKGROUND OF THE INVENTION

1. Field of the Invention

In general, the present invention relates to measurement devices used to properly fit eyeglasses. More particularly, the present invention relates to instruments used to determine the rear vertex distance between a lens and the eye.

2. Prior Art Description

When eyeglasses are created for a particular person, several measurements must be made. Many of those measurements depend upon the center of the pupils in relation to the lenses used in the eyeglasses. Eyeglasses can be either framed or frameless. Framed eyeglasses have lenses that are mounted on a frame. Frameless glasses have lenses that are only secured by a nosepiece and the ear handles of the eyeglasses.

When the wearer is at the opticians buying a new pair of eyeglasses, certain centering data has to be recorded in order to properly fit the lenses. This data is necessary for the grinding of the lenses and for fitting the lenses onto a frame. In order to ensure that the lenses correspond to the wearer's individual requirements, the manufacturers need to know a point on the lens directly in front of the pupil when the wearer is looking straight ahead and is said to have a natural posture and head position. When it comes to measuring the height of the middle of the pupil in relation to the lowest part of the spectacle frame, or in the case of frameless glasses in relation to the lowest part of the lens, the normal approach is that the optician will stand in front of the wearer and ask him or her to look straight ahead. At the same time, the wearer will be requested to take on a natural posture and head position. The optician will then try to sight the middle of the pupil and mark it on the lens using a felt marker. In the case of a new pair of spectacles, an optician will mark the demo glass.

Likewise, the optician needs to measure the rear vertex distance between the eyeglass lenses and the wearer's eyes. Each lens has a rear surface that faces the wearer. The rear vertex distance is the distance between the vertex of the cornea and the rear surface of the lens. Traditionally, this measurement is obtained by viewing or taking a picture of the wearer from the side. The measurement is then obtained using a ruler or by measuring the distance from the photograph.

There are a number of disadvantages associated with the traditional manner of measuring the center point on a lens and determining the rear vertex distance from this center point. If the wearer were to take on a body posture and head position that is different to his/her natural one, a wrong measurement can be recorded. For example, if the wearer tilts his/her head further back than normal, this causes him to look through a lower part of the lens in relation to the lowest part of the eyeglasses. The optician would then incorrectly sight the position of the middle of the pupil because of the wearer's unnatural posture and head position. If the lenses of the eyeglasses are made using this incorrect measurement, the eyeglasses would be incorrect. Furthermore, it often happens that a person will move his/her head between when the center of the lens is measured and when the rear vertex distance is measured. If the head moves between these measurements, the measurements will be adversely effected and the eyeglasses will be made incorrectly. Furthermore, if the measurement of the vertex distance is taken from the side, there will be parallax that makes the measurement inaccurate unless the patient's head is held firmly at 90° to the optician or the camera.

It has been observed that a person often holds his/her head in an unnatural position when being fitted for eyeglasses and/or while being photographed. When the optician stands near a person to take a pupil measurement or a photograph, that person often assumes a posture and head position that is different to his natural one. For example, a person may stand far more erect that he normally would. Alternatively, a person may tilt his head further back or forward than normal. The incorrect measurements may render the manufactured eyeglasses unusable, with the result that the optician has to redo the measurements and replace the lenses.

In the prior art, measurement devices have been developed that are used in the proper fitting of eyeglasses. For instance U.S. Pat. No. 4,505,043 to Sztuka, entitled Height Measurement Gage For Multifocal Lenses, a measurement device is shown that attaches to the frame of a pair of eyeglasses. The device records the position of the pupil relative the eyeglass frame. This eliminates the need to mark the lens with a felt marker. However, the device is only suitable with eyeglasses having specific angles of inclination. Furthermore, the device does not eliminate errors caused by taking measurements while a person's head is in an unnatural position. The device also requires that a separate side picture be taken in order to measure the rear vertex distance.

A need therefore exists for a device that can be used to accurately measure the position of a person's pupil in relation to a pair of eyeglasses, without having a person move his/her head from a natural position and posture. A need also exists for a system and method of measuring the rear vertex distance for a set of eyeglasses using an accurate center point and not requiring a separate side photograph for measurement. These needs are met by the present invention as described and claimed below.

SUMMARY OF THE INVENTION

The present invention is a measurement instrument and its associated method of use. The measurement instrument is used to record a pupil center position of a person's eye and to measure the rear vertex distance at that center position.

The instrument has a chassis and a free swinging assembly that is pivotably attached to the chassis. The swinging assembly has alignment points that remain in a horizontal plane as the swinging assembly swings. The instrument is attached to the set of eyeglasses that are being fitted for the patient. The eyeglasses and instrument are worn on that person's head. As a result, the instrument moves with the person's head and is affected by head position and posture.

While wearing the measuring instrument, a person is made to assume a natural head position for a specific activity. Once a natural head position is found, the swinging assembly is set into a locked position. Once in the locked position, the orientation between the alignment points and the chassis is set. The pupil center point can then be determined by observing the alignment points from a predetermined vantage point.

A prism is in front of the lens just adjacent to the pupil center point. As a result, a direct image of the pupil can be viewed through the lens. Likewise, a refracted image of the pupil can be viewed through the prism. The direct image and the refracted image are offset. The offset distance between the direct image and the refracted image is measured. The offset distance is a function of the rear vertex distance, thereby letting the rear vertex distance to be calculated.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

Figure 1:
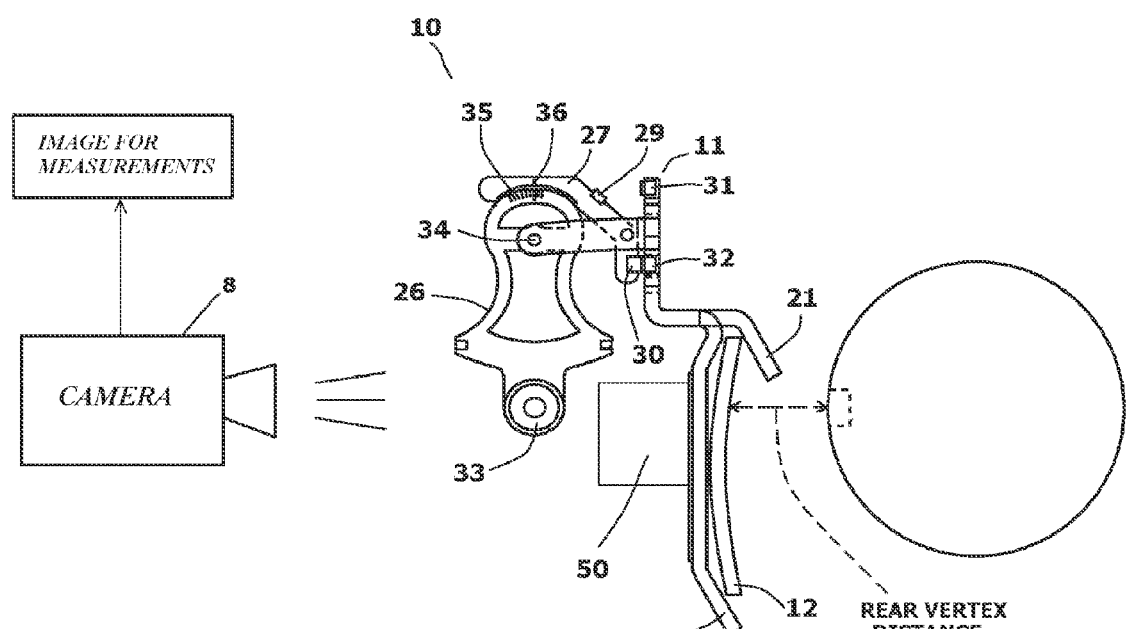
FIG. 1 is a side view schematic of an exemplary embodiment of the present invention system.

FIG. 1 shows an exemplary version of a measurement system 10. The system 10 utilizes a camera 8 to photograph a person wearing a measurement instrument 11. By using the measuring instrument 11, accurate measurements can be obtained from a single picture for both the natural center position of the eye and for the rear vertex distance. Since both measurements are taken from a single photograph, the measurements are simultaneous in time and are therefore not affected by movements of the head or eyes before or after the photograph is taken.

The camera 8 can be a film camera, a digital camera or even a video camera. The term photograph, as used in this system, is meant in the generic sense to represent any image recorded by the camera 11.

Figure 2:
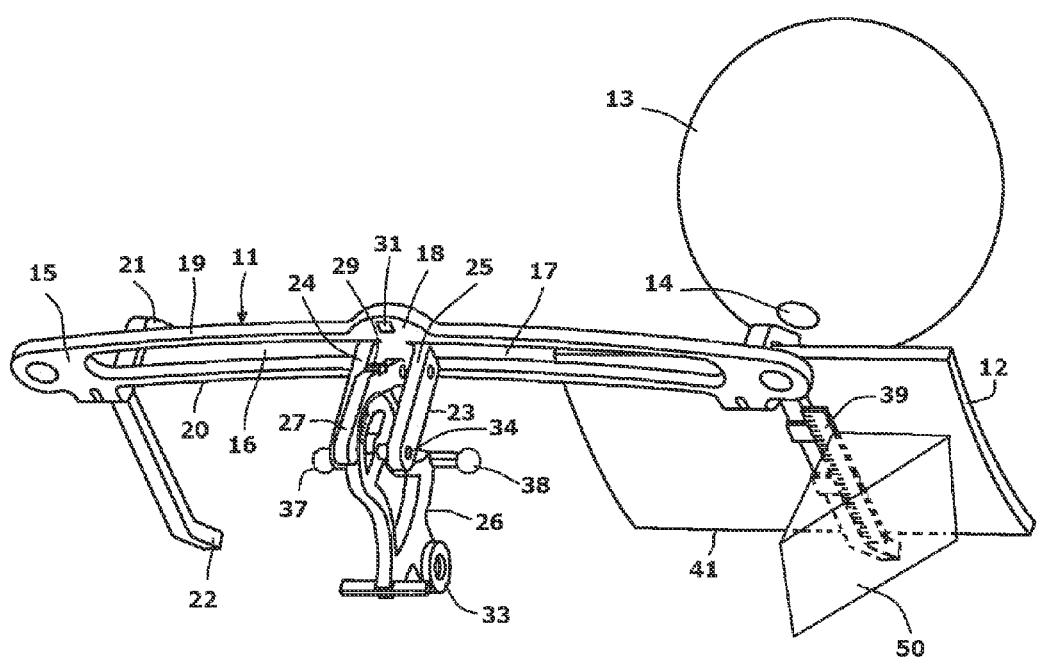
FIG. 2 is a perspective view of an exemplary measurement instrument used in the present invention system, shown in conjunction with a lens and a human eye.

Referring to FIG. 2 in accordance with FIG. 1, it can be seen that the measurement instrument 11 is shown in conjunction with schematic lens 12 which is to be measured in relation to the pupil 14 of a person's eye 13. The measurement instrument 11 has a chassis 15, which has an overall long stretched-out circular-arc shaped configuration. So as to save on weight, the chassis 15 can, for instance, be made of an aluminum alloy or of plastic materials and has two cut-outs 16, 17, which also serve the purpose of saving on weight. In the area between the two cut-outs 16, 17, the chassis 15 exhibits a plinth 18 which connects the over-bar 19 with the under-bar 20 of the chassis 15. In the area of the two distal ends of the chassis 15, two stays 21, 22 are present that form an inverted V-shape. The two stays 21, 22 include various angles so that they attach and support the measurement instrument 11 on the top of the eyeglass frames or lenses 12.

Using stays 21, 22, the measurement instrument 11 is attached to the lens 12 or the frame surrounding the lens 12, depending upon whether the eyeglasses are frameless or framed. The frame of the eyeglasses or the lenses 12 can be held between the stays 21, 22 at both distal ends of the measurement instrument 11 and in such a way that the measurement instrument 11 on the frame or, in the case of frameless spectacles, resting on the top of the two lenses, will not slip off.

The plinth 18 of the chassis 15 supports a fork assembly 23 that points from the chassis 15 at a right angle towards the front. The two forked arms 24, 25 create a space between them, the purpose of which is to hold a weighted swing assembly 26.

The weighted swing assembly 26 is shown in the locked position, brought about by a brake-arm 27, which pivots horizontally on a brake arm pin 28 and rests on the radius of the swing assembly 26.

On the side facing the plinth 18 and the chassis 15, the brake arm 27 holds a small permanent magnet 30 and mass 30 of magnetic material. The small permanent magnet 29 and magnetic mass 30 selectively connect to permanent magnets 31, 32 that are on the plinth 18. Depending upon the position of the brake-arm 27, the brake arm 27 can be moved into the locked position shown in the figures. Alternatively, the brake arm 27 can be moved into free position when the magnetic material 29 is brought into contact with the permanent magnet 31. In the free position, the brake-arm 27 is released from the locked position, in which it is in contact with the swing assembly 26, via a swing assembly weight 33. The weighted swing assembly 26 pivots on a transverse horizontal axel 34.

As is best shown in FIG. 2, the swing assembly 26 exhibits a degree scale 35 on the side facing the brake arm 27. The degree scale 35 enables the angle of inclination of the spectacle frame or lenses 12 to be recorded from a mark 36 envisaged on the brake-arm 27.

On the swing assembly 26 there are two optical reference points 37, 38. These reference points are preferably brightly colored circles or spheres.

Figure 3:
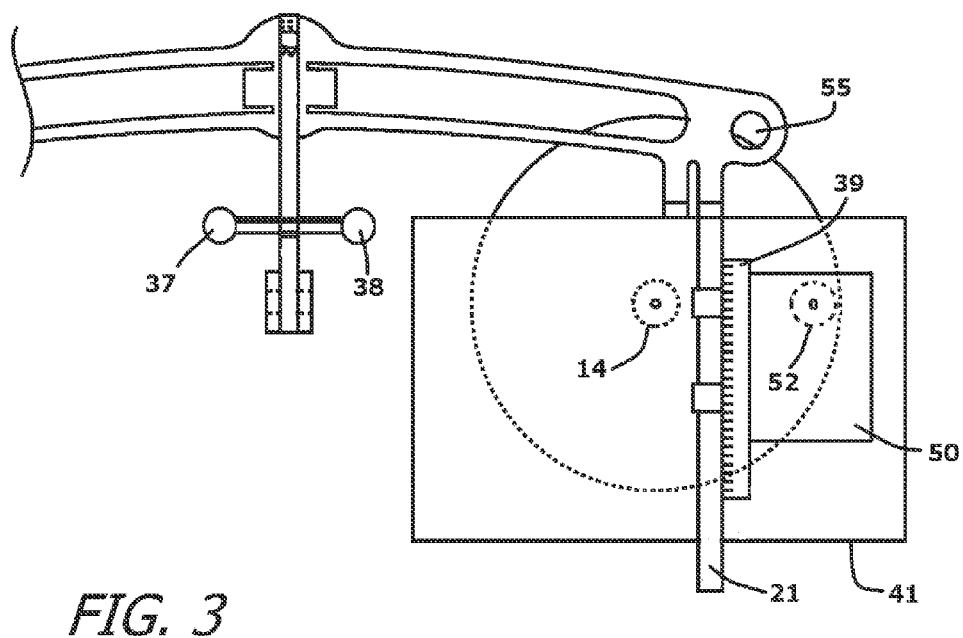
FIG. 3 is a partial front view of the exemplary measurement instrument embodiment of FIG. 2.

Referring to FIG. 3, it can be seen that a sliding measurement scale 39 is present on the lengthwise axial of the stay 21. The sliding measurement scale 39 can be shifted on the stay 21 so that the zero point of the measurement scale 39 can be brought into line with the lower rim 41 of the lens 12. Once positioned, the distance between the lower rim 41 and the pupil center 42 of the pupil 14 can be directly read off the measurement scale 39.

A prism 50 is affixed to the sliding measurement scale 39. The prism 50 creates an optical image 52 of the pupil and surrounding eye structure that is offset from the real pupil 14. As will be explained, the offset between the optical image 52 of the pupil and the real position of the pupil 14 is a function of the rear vertex distance. Accordingly, by viewing an image from the camera 8 (FIG. 1) that shows both the real position of the pupil 14 and the optical image 52 of the prism 50, the rear vertex distance can be measured.

Figure 4:
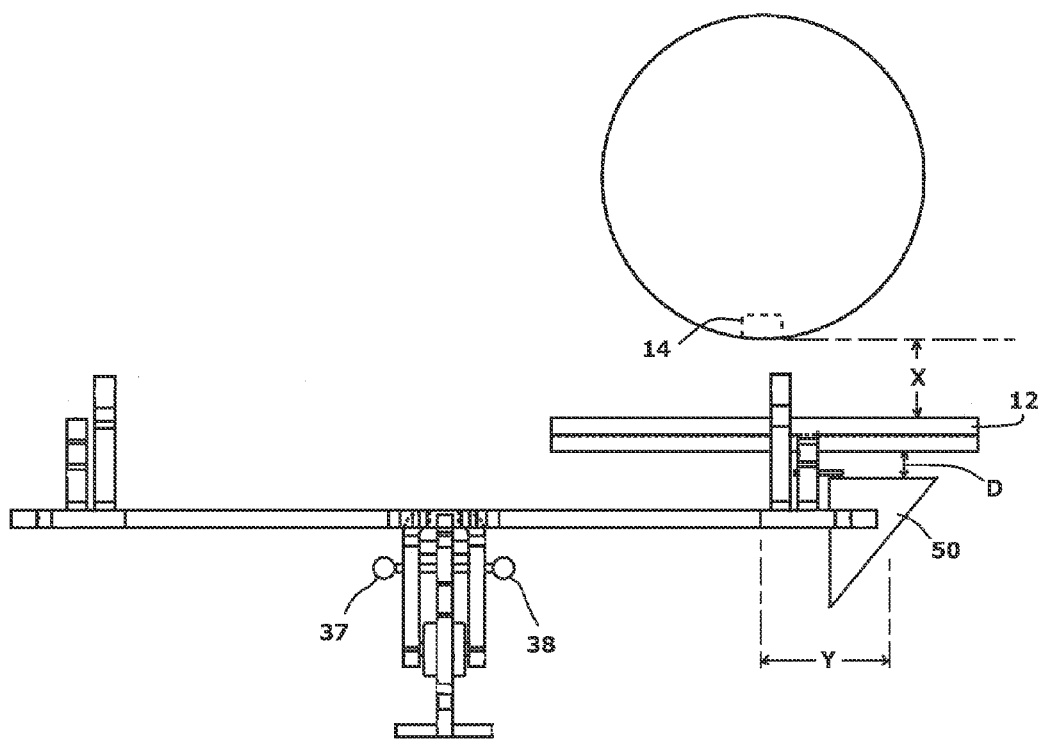
FIG. 4 is a top view of the exemplary measurement instrument embodiment of FIG. 2.

Referring to FIG. 4 in conjunction with FIG. 3, it can be seen that the prism 50 is positioned a known distance D from the lens 12 and an unknown distance X in front of the pupil 14. The unknown distance X is the rear vertex distance. The offset of the prism 50 is known or is directly measurable. The angles of the prism 50 are known as well as the optical properties of glass used to create the prism 50. The prism 50 creates an optical image 52 of the pupil that is offset from the real pupil 14 by a measurable distance Y, when viewed from the front. The measurable distance Y varies as a function of the sum (X+D) of the rear vertex distance X and the distance between the prism 50 and lens 12. By photographing the pupil 14 and the optical image 52 of the pupil, the measurable distance Y becomes known. Using the refraction angles of the prism 50 and simple trigonometry, the value for the rear vertex distance X can be calculated.

The optical reference points 37, 38 on the brake-arm 27 and optical reference points 55 on the chassis 15 can also be seen in a photograph. The size of the various optical reference points 37, 38, 55 and the distance between the optical reference points 37, 38, 55 is used to scale measurements made in the photograph. Accordingly, the camera need not be at any one set distance in front of the system.

Referring to FIGS. 1-5 in unison, it will be understood that to measure the distance between the lower rim 41 of the lens 12 and the pupil center 42, the instrument 11 is placed on the eyeglasses using stays 21, 22. The position of the brake-arm 27 is such that it is free to move having been released from its locked position in contact with the swing assembly 26 by flipping it up so that the two magnets 30, 32 are no longer in contact. In this free position, the brake-arm 27 is held by means of the magnetic material 29 and the permanent magnet 31 on the chassis 15 and the plinth 18. The customer wearing the eyeglasses and the instrument 11 is asked to assume a natural posture and head position and, in so doing, to focus on a point in the distance. The customer can do this standing in the shop, walking round the shop or looking at different points in the distance so that he assumes his own specific natural posture and head position which he will also assume when, at a later date, he wears the eyeglasses that are about to be custom-made for him.

In addition to the above-mentioned alternatives, the wearer can also assume a different position. A wearer can, for instance, sit in a car, at a desk or in front of a computer screen so that with the help of the measurement instrument 1 it is possible to produce eyeglasses for a specific use that relate to the posture and head position assumed by the wearer when carrying out the specific activity.

The swing assembly 26 does not actually follow the movements of the head, and the body of the wearer, but rather pivots on the axel 34 in relation to the chassis 15. The wearer's horizontal line of sight is specific to the wearing and depends upon the position and activity of the wearer. A wearer may therefore have different lines of sight when driving and when walking.

Since, while the wearer's horizontal line of sight is being recorded as a photograph, the customer is not being disturbed by, for instance, the optician standing in front of him. Rather, the wearer assumes a natural posture and head position The wearer's natural posture and head position can be determined by the optician, or a member of his staff and, for instance, assessed while talking to the wearer in the shop. Once a natural posture and head position is photographed, the optician, or a member of his staff, can release the brake arm 27. The brake arm 27 is preferably released from the side, or from behind, so that the wearer is not disturbed in any way and continues to assume his natural posture and head position. Once the brake arm 27 is released, the permanent magnet 30 comes into contact with permanent magnet 32 and the horizontal line of sight specific to the wearer is captured and recorded by means of the contact between the brake-arm 27 and the horizontal swing assembly 26.

The height of the pupil 14 in relation to the lower rim 41 of the lens 12 is then calculated on the basis of the wearer's horizontal line of sight as determined above. For this purpose, the optician, or a member of his staff, can ask the wearer to sit down and then take a photograph. Doing this will not change the wearer's recorded horizontal line of sight because contact exists between the brake-arm 27 and the swing assembly 26 prevents the swing assembly 26 from moving out of its locked position.

Referring back to FIGS. 1-3, it can be seen to utilize the measurement instrument 11, the measurement instrument 11 is attached to a pair of eyeglasses. The eyeglasses are then worn by a person. As the measurement instrument 11 is being worn, the weighted swing assembly 16 pivots freely on the horizontal rotational axis such that a plane created by the swing assembly 16 always runs perpendicular to the wearer's horizontal line of sight even when the wearer changes his posture or head position. In other words, with the help of the freely pivoting swing assembly 26, a plane is created which follows the wearer's horizontal line of sight as he/she assumes different posture and head positions.

The horizontal plane that is created follows the horizontal line of sight of the wearer. When, for example, the wearer walks around having assumed a posture and head position that is comfortable and therefore natural for him when looking into the distance, the horizontal plane created by the alignment planes always runs parallel to the horizontal line of sight of the wearer, whereby the distance between the parallels can be zero.

The horizontal plane that corresponds to the natural line of sight for the wearer is determined by viewing various reference point on the swing assembly 26. The method of determining the natural line of sight is described in co-pending U.S. patent application Ser. No. 11/210,450, entitled, Device And Method For Determining The Height Of The Middle Of The Pupil In Relation To The Lowest Part Of A Pair Of Eyeglasses.

The swing assembly 26 is locked into place one it has been aligned with the wearer's natural line of site. With the swing assembly 26 locked into place, the prism 50 is adjusted into position and a photograph is taken. Once the wearer's horizontal line of sight and the prism 50 offset have been captured and recorded, the wearer's horizontal line of sight no longer changes. The rear vertex distance and the center of the lenses can then be directly measured from the recorded photograph.

It will be understood that the embodiment of the present invention measurement instrument that is illustrated is merely exemplary and that many features of the instrument can be redesigned in manners that are functionally equivalent. All such variations, modifications and alternate embodiments are intended to be included within the scope of the present invention as claimed.

What is claimed is:

1. A method of determining the rear vertex distance between a lens in a set of eyeglasses and the cornea covering the pupil of an eye, said method comprising the steps of:
   providing a set of eyeglasses having a lens;
   providing a prism that is separate and distinct from said lens;
   mounting said prism in front of said lens;
   viewing a direct image of said pupil through only said lens;
   viewing a refracted image of said pupil through both said lens and said prism; and
   measuring an offset distance between said direct image and said refracted image, wherein said offset distance is a function of said rear vertex distance.

2. The method according to claim 1, further including the step of determining a center position of said pupil relative to said lens prior to viewing said direct image of said pupil.

3. The method according to claim 1, further including the step of taking a photograph that contains both said direct image and said refracted image.

4. The method according to claim 3, wherein said step of measuring an offset distance includes measuring said offset distance from said photograph.

5. The method according to claim 2, wherein said step of determining a center position of said pupil includes the substeps of:
   providing an instrument that has a chassis and a free swinging assembly that is pivotably attached to said chassis;
   attaching said instrument to a person's head so that said instrument moves with the person's head;

having the person assume a natural head position for a specific activity;

locking said swinging assembly into a locked position when said head is in said natural head position; and determining the pupil center point of the person by observing said instrument in said locked position.

6. The method according to claim 5, wherein said step of attaching said instrument to a person's head includes providing eyeglasses, placing said eyeglasses on a person's head and attaching said instrument to said eyeglasses.

7. The method according to claim 5, wherein said step of attaching said instrument to a person's head includes providing eyeglasses, placing said eyeglasses on a person's head and attaching said instrument to said eyeglasses, wherein said eyeglasses has a lens element positioned in front of said pupil center point.

8. The method according to claim 5, wherein said step of mounting a prism in front of said lens includes mounting said prism to said instrument.

9. A method of determining the rear vertex distance between a lens in a set of eyeglasses and the cornea covering the pupil of an eye, said method comprising the steps of:

providing eyeglasses having at least one lens;

providing an instrument that attached to said eyeglasses, wherein said instrument supports a prism that is separate and distinct from said at least one lens of said eyeglasses;

attaching said instrument to a person's head by wearing said eyeglasses, wherein said instrument moves with the person's head;

viewing a direct image of said pupil through only said lens;

viewing a refracted image of said pupil through both said lens and said prism;

measuring an offset distance between said direct image and said refracted image; and calculating said rear vertex distance from said off set distance.

10. The method according to claim 9, further including the step of determining a center position of said pupil relative said lens prior to viewing said direct image of said pupil.

11. The method according to claim 9, further including the step of taking a photograph that contains both said direct image and said refracted image.

12. The method according to claim 11, wherein said step of measuring an offset distance includes measuring said offset distance from said photograph.

13. The method according to claim 10, wherein said step of determining a center position of said pupil includes the sub-steps of:

having the person assume a natural head position for a specific activity;

locking said swinging assembly into a locked position when said head is in said natural head position; and determining the pupil center point of the person by observing said instrument in said locked position.

14. A method of determining the rear vertex distance between a lens in a set of eyeglasses and the cornea covering the pupil of an eye, said method comprising the steps of:

providing eyeglasses having at least one lens;

providing a prism that is separate and distinct from said at least one lens;

mounting a prism to said eyeglasses;

attaching said prism to a person's head by wearing said eyeglasses;

viewing a direct image of said pupil through said at least one lens;

viewing a refracted image of said pupil through both said at least one lens and said prism;

measuring an offset distance between said direct image and said refracted image; and calculating said rear vertex distance from said off set distance.

* * * * *